US012599434B2

(12) United States Patent
Akerele-Ale et al.

(10) Patent No.: US 12,599,434 B2
(45) Date of Patent: Apr. 14, 2026

(54) CATHETER SYSTEMS WITH BIASING RAILS AND METHODS FOR FORMING FISTULAS

(71) Applicant: TVA Medical, Inc., Franklin Lakes, NJ (US)

(72) Inventors: Oladipo Peter Akerele-Ale, Phoenix, AZ (US); Andrew Moll, Portland, OR (US); Alex Palmer, Gilbert, AZ (US); Breanna Simpson, Austin, TX (US); Olivia Ruth Palmer, Nashville, TN (US)

(73) Assignee: TVA Medical, Inc., Franklin Lakes, NJ (US)

( * ) Notice: Subject to any disclaimer, the term of this patent is extended or adjusted under 35 U.S.C. 154(b) by 504 days.

(21) Appl. No.: 18/254,734

(22) PCT Filed: Nov. 30, 2020

(86) PCT No.: PCT/US2020/062556
§ 371 (c)(1),
(2) Date: May 26, 2023

(87) PCT Pub. No.: WO2022/115109
PCT Pub. Date: Jun. 2, 2022

(65) Prior Publication Data
US 2023/0404659 A1     Dec. 21, 2023

(51) Int. Cl.
*A61B 18/14*       (2006.01)
*A61B 17/11*       (2006.01)
(Continued)

(52) U.S. Cl.
CPC .......... *A61B 18/1492* (2013.01); *A61B 34/73* (2016.02); *A61B 2017/1107* (2013.01);
(Continued)

(58) Field of Classification Search
None
See application file for complete search history.

(56) References Cited

U.S. PATENT DOCUMENTS

| | | | |
|---|---|---|---|
| 5,782,239 A | 7/1998 | Webster, Jr. | |
| 5,836,947 A * | 11/1998 | Fleischman | ........ A61B 18/1492 |
| | | | 606/41 |

(Continued)

FOREIGN PATENT DOCUMENTS

| | | |
|---|---|---|
| WO | 1997033522 A1 | 9/1997 |
| WO | 9824372 W | 6/1998 |

(Continued)

OTHER PUBLICATIONS

International Search Report and Written Opinion dated Aug. 25, 2021 as received in PCT/US2020/062556.

*Primary Examiner* — Linda C Dvorak
*Assistant Examiner* — Nicholas S Borsch
(74) *Attorney, Agent, or Firm* — Dickinson Wright PLLC; Andrew D. Dorisio

(57) ABSTRACT

A system for forming a fistula, including a catheter including a catheter body, an electrode, one or more arrays of magnets, and a plurality of biasing rails. The one or more arrays of magnets are arranged longitudinally along the catheter body. The plurality of biasing rails extend along a length of the catheter body and are configured to radially arch away from the catheter body between a proximal point positioned proximal a first end of at least one array of magnets and a distal point positioned distal to a second end of the at least one array of magnets. The plurality of biasing rails bias the working site and the one or more arrays of magnets against a blood vessel wall. The plurality of biasing rails are joined by a connecting rail that laterally extends between the plurality of biasing rails.

30 Claims, 6 Drawing Sheets

(51) Int. Cl.
    *A61B 18/00*         (2006.01)
    *A61B 34/00*         (2016.01)

(52) U.S. Cl.
    CPC ................. *A61B 2017/1139* (2013.01); *A61B 2018/00404* (2013.01); *A61B 2018/00577* (2013.01); *A61B 2018/00601* (2013.01); *A61B 2018/1407* (2013.01); *A61B 2034/731* (2016.02)

(56)             References Cited

U.S. PATENT DOCUMENTS

| | | | |
|---|---|---|---|
| 6,071,274 | A | 6/2000 | Thompson |
| 6,629,987 | B1 | 10/2003 | Gambale |
| 6,726,677 | B1 | 4/2004 | Flaherty |
| 7,522,950 | B2 | 4/2009 | Fuimaono |
| 9,017,323 | B2 * | 4/2015 | Miller ................... A61B 18/16 606/41 |
| 9,039,702 | B2 | 5/2015 | Miller |
| 9,486,276 | B2 | 11/2016 | Rios |
| 9,510,901 | B2 | 12/2016 | Steinke |
| 11,026,743 | B2 | 6/2021 | Pate |
| 11,826,093 | B2 | 11/2023 | Pate |
| 2007/0203515 | A1 | 8/2007 | Heuser |
| 2014/0012251 | A1 | 1/2014 | Himmelstein |
| 2017/0020216 | A1 | 1/2017 | Yamada |
| 2018/0344396 | A1 | 12/2018 | Miller |
| 2020/0038103 | A1 | 2/2020 | Pappone |
| 2020/0178970 | A1 | 6/2020 | Berman |

FOREIGN PATENT DOCUMENTS

| | | | |
|---|---|---|---|
| WO | 2012068273 | A1 | 5/2012 |
| WO | 2014028306 | A1 | 2/2014 |
| WO | 2016090175 | A1 | 6/2016 |

* cited by examiner

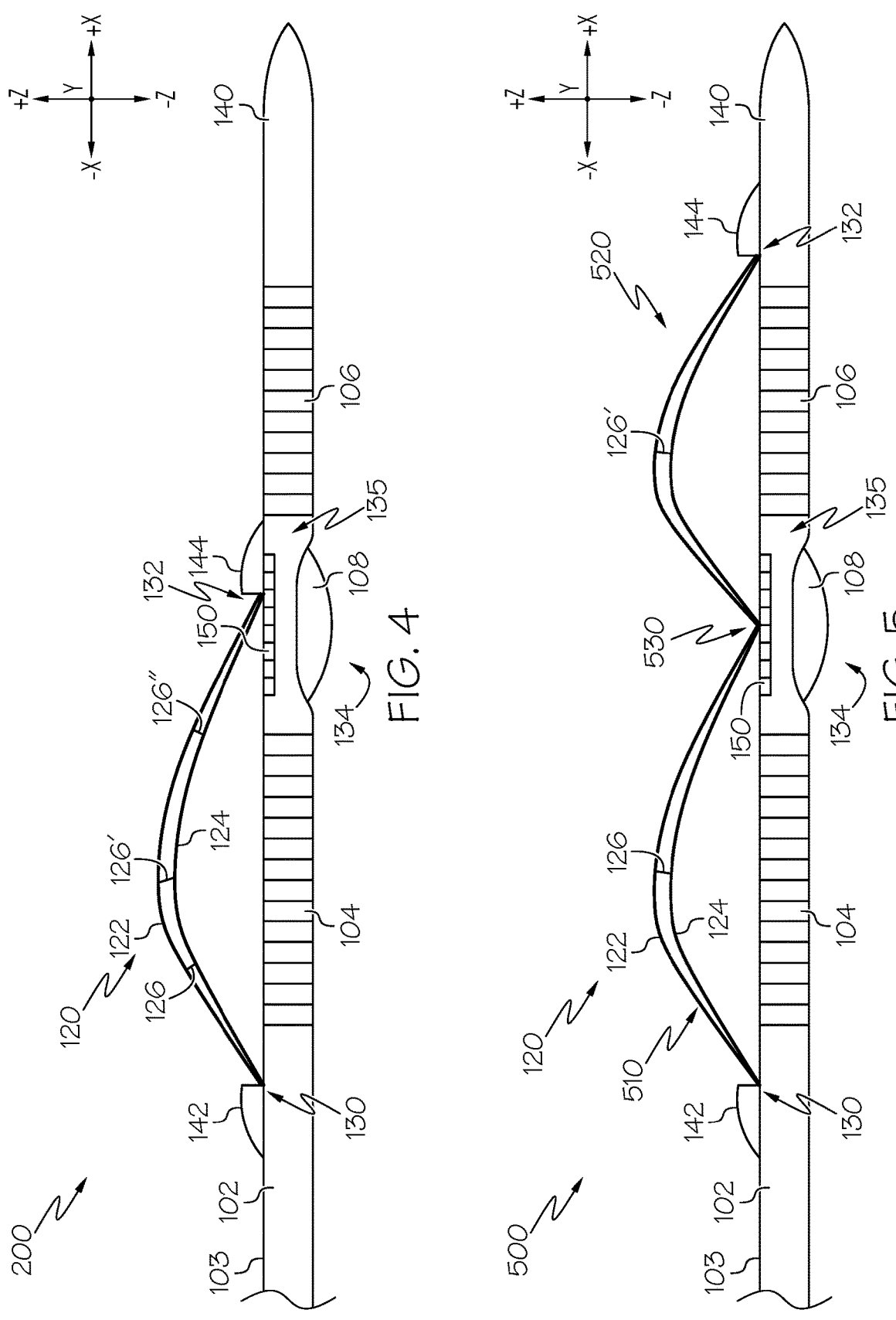

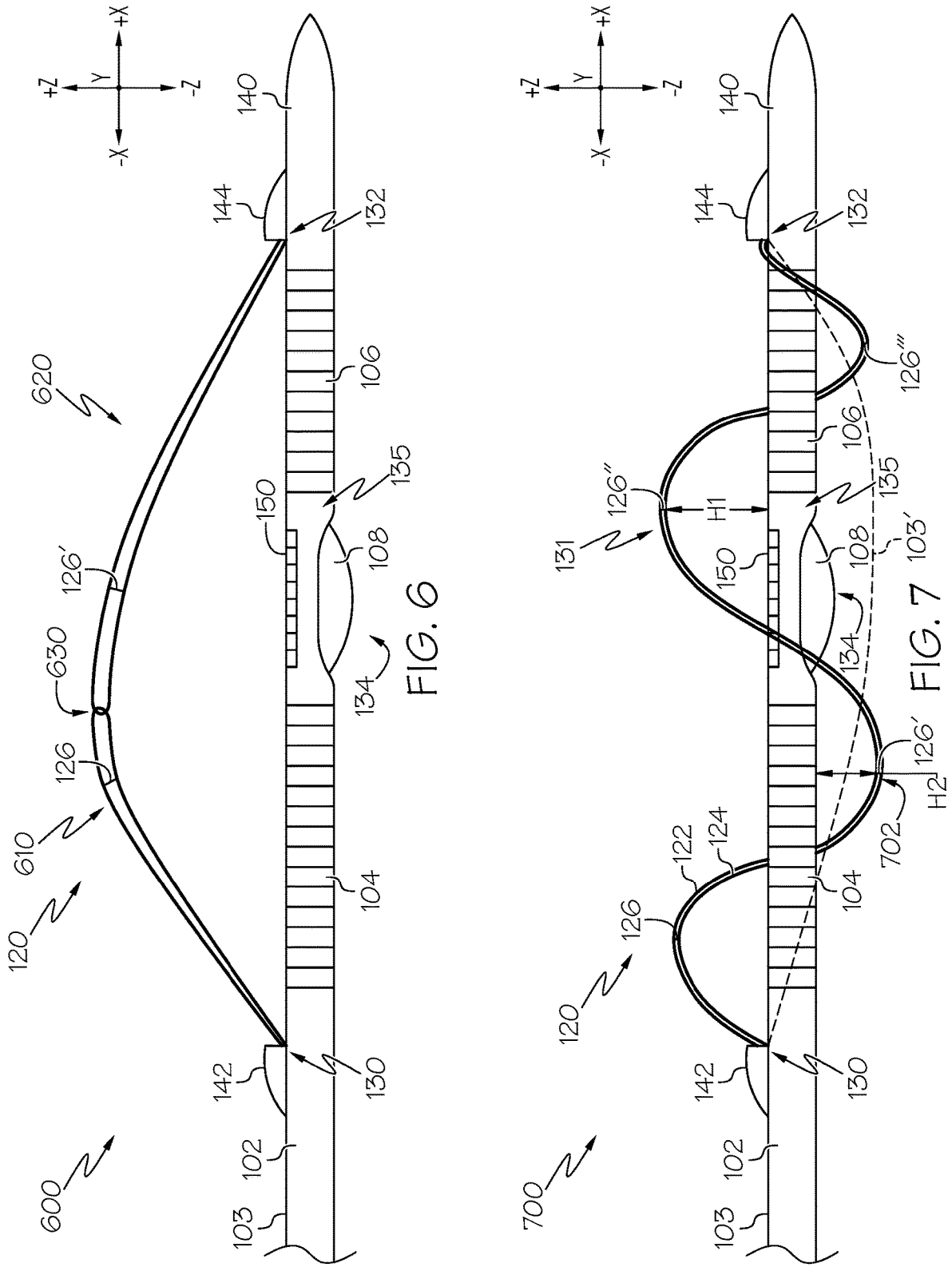

CATHETER SYSTEMS WITH BIASING RAILS AND METHODS FOR FORMING FISTULAS

TECHNICAL FIELD

The present disclosure relates to devices and methods for forming a fistula, and more particularly devices and methods with integrated biasing rails for biasing the device into contact with a vessel for fistula formation.

BACKGROUND

A fistula is generally a passageway formed between two internal organs. Forming a fistula between two blood vessels can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. In other instances, a fistula may be formed between two veins to form a veno-venous fistula. Generally, fistula formation requires surgical dissection of a target vein, and transecting and moving the vein for surgical anastomosis to the artery. It may therefore be useful to find less invasive and reliable devices and methods for forming a fistula between two blood vessels.

SUMMARY

One challenging aspect of forming a fistula between blood vessels, though other body vessels are contemplated and possible, is properly aligning and coapting catheters in adjacent blood vessels prior to fistula formation. Accordingly, a need exists for alternative systems, methods, and catheters for fistula formation that ensure catheter alignment and coaptation. Embodiments of the present disclosure are directed to improvements over the above limitations by providing biasing rails which bias the catheter into proper alignment.

In one embodiment, a system for forming a fistula between two blood vessels, including a first catheter including a first catheter body, an electrode, one or more arrays of magnets, and a first plurality of biasing rails. The electrode is configured to project from a working site of the first catheter and define an active side of the first catheter. The one or more arrays of magnets are arranged longitudinally along the first catheter body. The first plurality of biasing rails longitudinally extend along a length of the first catheter body and are configured to radially arch away from the first catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets. The first plurality of biasing rails extend from a non-active side of the first catheter body such that the first plurality of biasing rails are configured to bias the working site and the one or more arrays of magnets against a first blood vessel wall. The first plurality of biasing rails are joined by a connecting rail that laterally extends between the first plurality of biasing rails at a point between the proximal point and the distal point.

In another embodiment, a method of forming a fistula between a first blood vessel and a second blood vessel, including advancing a first catheter into the first blood vessel. The first catheter includes a first catheter body, an electrode, one or more arrays of magnets, and a first plurality of biasing rails. The electrode is configured to project from a working site of the first catheter and define an active side of the first catheter. The one or more arrays of magnets are arranged longitudinally along the first catheter body. The first plurality of biasing rails longitudinally extend along a length of the first catheter body and are configured to radially arch away from the first catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets. The first plurality of biasing rails extend from a non-active side of the first catheter body such that the first plurality of biasing rails are configured to bias the working site and the one or more arrays of magnets against a first blood vessel wall. The method further includes ablating tissue with the electrode to form the fistula.

In yet another embodiment, a system for forming a fistula between two blood vessels, including a first catheter. The first catheter includes a catheter body, an electrode, one or more arrays of magnets, and a plurality of biasing rails. The electrode is configured to project from a working site of the first catheter and define an active side of the first catheter. The one or more arrays of magnets are arranged longitudinally along the catheter body. The plurality of biasing rails longitudinally extend along a length of the catheter body. The plurality of biasing rails are configured to radially arch away from the catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets. The plurality of biasing rails extend from a non-active side of the catheter body such that the plurality of biasing rails are configured to bias the working site and the one or more arrays of magnets against a first blood vessel wall. The plurality of biasing rails are joined by a connecting rail that laterally extends between the plurality of biasing rails at a point between the proximal point and the distal point. The plurality of biasing rails include a proximal portion extending through a lumen of the catheter body. The proximal portion may be advanced in the lumen to transition the plurality of biasing rails to an extended configuration, wherein the plurality of biasing rails radially arch away from the catheter body; and the proximal portion may be retracted in the lumen to transition the plurality of biasing rails to a low-profile configuration, wherein a maximum distance of radial deflection of the plurality of biasing rails is less than a maximum distance of radial deflection of the plurality of biasing rails in the extended configuration.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 4 schematically depicts a side view of another catheter, according to one or more embodiments shown and described herein;

FIG. 5 schematically depicts a side view of a another catheter, according to one or more embodiments shown and described herein;

FIG. 6 schematically depicts a side view of another catheter, according to one or more embodiments shown and described herein; and FIG. 7 schematically depicts a side view of another catheter, according to one or more embodiments shown and described herein.

DETAILED DESCRIPTION

Embodiments described herein are directed to devices and methods for forming a fistula. In some embodiments, the devices and methods may be used to form a fistula between two blood vessels. More particularly, a catheter may be placed in each of two adjacent blood vessels to form a fistula therebetween with the catheters.

Fistula forming elements may be mounted to catheters which may then be used to form a fistula between vessels. However, flexibility of the catheters, spacing of vessels, thickness of the vessel walls, and/or the tortuous anatomy of the vessels, may make it difficult to provide sufficient coaptation and/or alignment between vessels for fistula formation. The embodiments described herein address the one or more aforementioned limitations. In particular, the devices and methods for forming a fistula described herein may include a catheter having a catheter body, an electrode, one or more arrays of magnets, and a plurality of biasing rails. The electrode may be configured to project from a working site of the catheter and define an active side of the catheter. The plurality of biasing rails extend longitudinally along a length of the catheter body and are configured to radially arch away from the catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets. The plurality of biasing rails may be joined by a connecting rail that extends laterally between the plurality of biasing rails at a point between the proximal point and the distal point. The plurality of biasing rails extend from a non-active side of the catheter body such that the plurality of biasing rails are configured to bias the working site and/or the one or more arrays of magnets against a blood vessel wall. Accordingly, the plurality of biasing rails promote positioning of the one or more arrays of magnets against the blood vessel wall to allow better magnetic attraction between the one or more arrays of magnets of the catheter and one or more arrays of magnets attached to a second catheter, which may be positioned in a second blood vessel adjacent to the blood vessel. Therefore, the plurality of biasing rails in conjunction with the one or more arrays of magnets may align and closely approximate the first and second catheters in adjacent blood vessels, allowing for more reliable fistula formation between the first and second blood vessels. Various embodiments will now be described in greater detail below with reference to the figures.

Figures 1A, 1B:
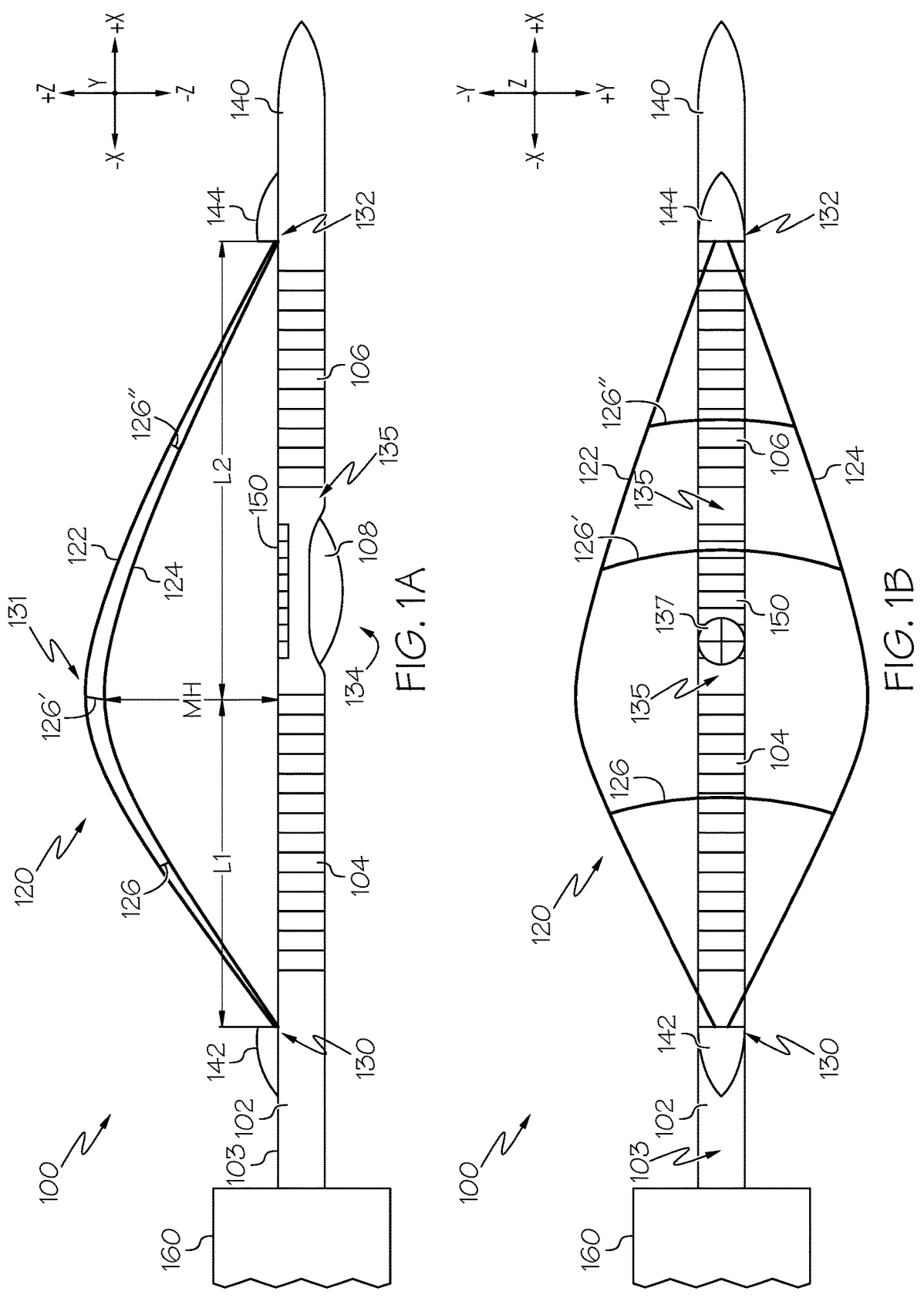
FIG. 1A schematically depicts a side view of a catheter, according to one or more embodiments shown and described herein.
FIG. 1B schematically depicts a top view of the catheter of FIG. 1A, according to one or more embodiments shown and described herein.
Figures 3A, 3B:
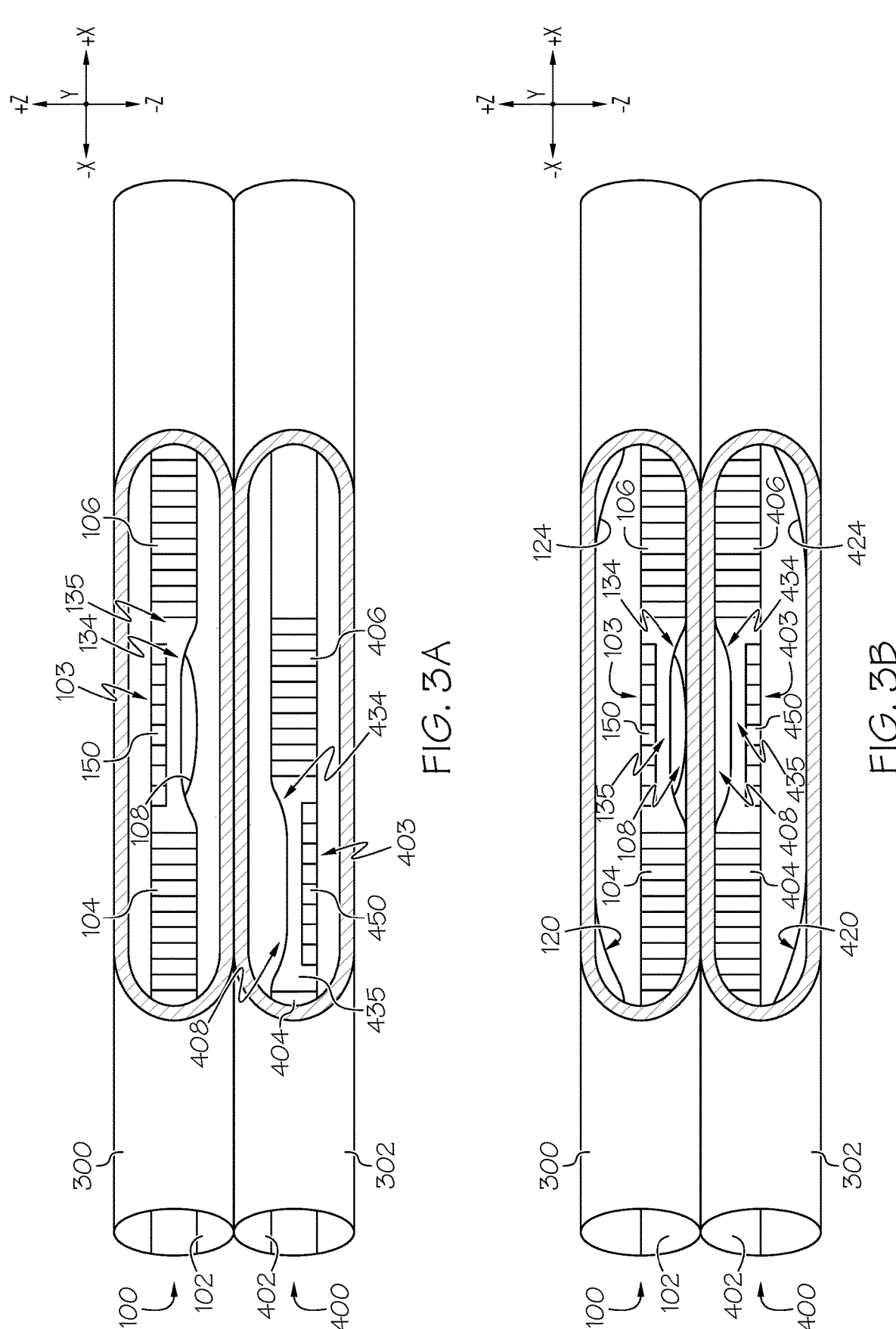
FIG. 3A schematically depicts a two catheter system, according to one or more embodiments shown and described herein.
FIG. 3B schematically depicts a two catheter system, according to one or more embodiments shown and described herein.

Referring now to FIG. 1A, a catheter 100 (e.g., a first catheter) of a system for forming a fistula is depicted. As will be described in greater detail herein, the system may further include a second catheter 400 (FIG. 3A). While the structure of the first catheter 100 will be discussed in detail, it should be appreciated that the structure of the second catheter 400 (FIG. 3A) may mirror the first catheter 100 except where noted. The catheter 100 generally includes a catheter body 102, which may include a distal tip 140 that is particularly configured to aid in advancement of the catheter 100 through a blood vessel. For example, the distal tip 140 may be pointed and/or atraumatic for advancement through a blood vessel. The catheter body 102 may have any desirable cross-sectional shape and any suitable diameter for intravascular use. The catheter 100 may further include one or more lumens or other passageways extending at least partially along or through the catheter body 102. For instance, the one or more lumens may extend at least partially longitudinally through the catheter body 102 in the direction of the x-axis of the coordinate axes of FIG. 1A.

The catheter 100 may further include a working site 135 arranged along the catheter body 102. The working site 135, as described herein, refers to a portion of the catheter 100 positioned along the catheter body 102 that is configured to modify a blood vessel (e.g., cut, ablate, etc.). In particular, in embodiments of the present disclosure, the catheter 100 may include a working site 135 that is configured to form one or more fistulas between a first blood vessel 300 (FIG. 3A) and a second blood vessel 302 (FIG. 3A). In embodiments, the working site 135 may be positioned along the catheter body 102 at a position proximal to (e.g. in the −x direction of the coordinate axes of FIG. 1A) the distal tip 140 and define an active side 134. The working site 135 may comprise one or more openings in the active side 134 of the working site 135 that allow for passage of one or more instruments into and/or out of the catheter body 102 for modifying the vessel. For example, the active side 134 of the working site 135 is the portion of the working site 135 that abuts or faces the area of the vessel where a modification is to be made. For instance, an electrode 108 may protrude from the active side 134 of the working site 135 and extend radially away from a longitudinal centerline of the catheter 100 to contact a wall of the blood vessel 300 (see e.g., FIG. 3B).

The electrode 108 may include an exposed ablation surface, which may be activated to ablate tissue, and a lead wire or other conductor attached thereto. Particularly, when activated, current may be supplied to and/or carried from tissue and fluid via the ablation surface to facilitate ablation or vaporization of tissue to form a fistula. In some embodiments, the electrode 108 may be a spring wire or leaf spring electrode, which may be movable between a retracted configuration, in which the electrode 108 is retained within the catheter 100, and a protruding configuration, in which electrode 108 projects from a surface of the catheter body 102. The electrode 108 may or may not be naturally biased to project from the catheter body 102. When the electrode 108 is naturally biased to project from the catheter body 102, a structure, such as a sleeve 160, may be used to hold or maintain the electrode 108 in a retracted configuration until deployment is desired. In some embodiments, the catheter body 102 may comprise one or more insulating materials (not shown) which may shield or otherwise protect the catheter 100 and its components from heat generated by the electrode 108 during use.

Still referring to FIG. 1A, the catheter 100 includes a non-active side 103 or region positioned opposite the active side 134 of the working site 135. For example, the non-active side 103 refers to the side of the catheter 100 devoid of cutting and/or ablation means. The non-active side 103 of the catheter 100 extends across the catheter body 102 and the working site 135. In other words, the catheter body 102 and the working site 135 may both define the non-active side 103. The non-active side 103 of the catheter body 102 and working site 135 is diametrically opposite the active side 134 of the working site 135. Therefore, the non-active side 103 of the catheter body 102 and working site 135 is positioned opposite the electrode 108. In other words, the non-active side 103 of the catheter body 102 and working site 135, does not abut or face a modification being formed in the blood vessel 300 (FIG. 3A) via the active side 134 of the working site 135. Instead the non-active side 103 of the catheter body 100 may be spaced from a modification being formed in the blood vessel 300 (FIG. 3A) by the electrode 108 by the diameter or height (e.g. in the direction of the z-axis of the coordinate axes of FIG. 1A) of at least a portion of the catheter body 102.

Still referring to FIG. 1A, the catheter 100 may include one or more arrays of magnets arranged longitudinally along the catheter body 102. For instance, the catheter 100 may include a first array of magnets 104 that extends longitudinally along the catheter body 102 and is positioned proximal (e.g. in the −x direction of the coordinate axes of FIG. 1A) to the working site 135. The catheter 100 may include a second array of magnets 106 that extends longitudinally along the catheter body 102 and is positioned distal (e.g. in the +x direction of the coordinate axes of FIG. 1A) to the working site 135. In some embodiments, the second array of magnets 106 may be positioned longitudinally between (e.g. in the direction of the x-axis of the coordinate axes of FIG. 1A) the working site 135 and the distal tip 140 of the catheter body 102. In embodiments, the catheter 100 may include a third array of magnets 150 positioned in the working site 135 behind the active side 134 of the working site 135. More particularly, the third array of magnets 150 may be positioned along and/or within the non-active side 103 of the working site 135. In embodiments, the catheter 100 may include the first array of magnets 104, the second array of magnets 106, and the third array of magnets 150 individually or in any combination. It should be appreciated that while the phrase "array of magnets" is used herein, that each of the arrays of magnets 104, 106, and 150 may be configured as a single magnet along the catheter body 102 and/or working site 135.

The arrays of magnets 104, 106, and 150 described herein may be permanent magnets comprising one or more hard magnetic materials, such as but not limited to alloys of rare earth elements (e.g., samarium-cobalt magnets or neodymium magnets, such as N52 magnets) or alnico. In some variations, the arrays of magnets 104, 106, and 150 may comprise anisotropic magnets; in other variations, the arrays of magnets 104, 106, and 150 may comprise isotropic magnetics. In some variations, the arrays of magnets 104, 106, and 150 may be formed from compressed powder. In some variations, a portion of the arrays of magnets 104, 106, and 150 (e.g., a permeable backing) may comprise one or more soft magnetic materials, such as but not limited to iron, cobalt, nickel, or ferrite. It should be appreciated that in systems comprising two catheters, either the first catheter 100 or the second catheter 400 (FIGS. 3A and 3B) may comprise ferromagnetic elements (i.e., elements attracted to but not generating a permanent magnetic field). For example, in some variations, the first catheter 100 may include only one or more ferromagnetic elements while the second catheter 400 (FIGS. 3A and 3B) may comprise one or more permanent magnets. In other variations, the second catheter 400 (FIGS. 3A and 3B) may include only one or more ferromagnetic elements while the first catheter 100 may comprise one or more permanent magnets. However, in other variations, one or both of the first catheter 100 and the second catheter 400 (FIGS. 3A and 3B) may include any suitable combination of ferromagnetic, permanent, and/or other suitable kinds of magnets.

Generally, the dimensions of the arrays of magnets 104, 106, and 150 described herein may be selected based upon by the size of the catheter 100 carrying the arrays of magnets 104, 106, and 150, which in turn may be selected based upon the anatomical dimensions of the selected blood vessels through which the catheter 100 may be advanced. For example, if the catheter 100 is to be advanced through a blood vessel 300 (FIGS. 3A and 3B) having an internal diameter of about 3 mm, it may be desirable to configure any array of magnets 104, 106, and 150 to be less than about 3 mm at the widest part of their cross-sections, to reduce the risk of injury to vessel walls during advancement and manipulation of the catheter 100. Each array of magnets 104, 106, and 150 may have any suitable length (e.g., about 5 mm, about 10 mm, about mm, about 20 mm, and the like), although it should be appreciated that in some instances longer arrays of magnets may limit the flexibility of the catheter 100 to maneuver through a vessel. In some variations, the arrays of magnets 104, 106, and 150 may include a plurality of square magnets. In other embodiments, each magnet of the arrays of magnets 104, 106, and 150 may have any suitable shape for placement inside or outside of the catheter. Magnets may be cylindrical, semi-cylindrical, tube-shaped, box-shaped, or the like.

In embodiments, the outer surfaces of the arrays of magnets 104, 106, and 150 may be flush or in line with the outer surface of the catheter body 102. In other embodiments, the magnets 104, 106, and 150 may be positioned radially within the catheter body 102 away from the outer surface of the catheter body 102. In other embodiments the outer surfaces of the arrays of magnets 104, 106, and 150 may extend a distance radially beyond the outer surface of the catheter body 102.

Each array of magnets 104, 106, 150 may be fixed in or on the catheter 100 by any suitable method. For example, in some variations the one or more arrays of magnets 104, 106, and 150 may be embedded in, adhered to, or friction-fit within the catheter 100.

Still referring to FIG. 1A, the catheter 100 may further include one or more biasing rails. In embodiments the catheter 100 may include a plurality of biasing rails 120 that includes a first biasing rail 122 and a second biasing rail 124. While the plurality of biasing rails 120 are discussed as a pair of biasing rails 122, 124, it should be appreciated that the plurality of biasing rails 120 may include any number of biasing rails. The plurality of biasing rails 120 may extend longitudinally (e.g. in the direction of the x-axis of the coordinate axes of FIG. 1A) along a length of the catheter body 102. The plurality of biasing rails 120 may arch radially away from the catheter body 102 between a proximal point 130 and a distal point 132 of the catheter body 102. The proximal point 130 may be positioned proximal (e.g. in the −x direction of the coordinate axes of FIG. 1A) a first end of at least one array of the arrays of magnets 104, 106, 150, and the distal point 132 may be positioned distal (e.g. in the +x direction of the coordinate axes of FIG. 1A) a second end of the at least one array of the arrays of magnets 104, 106, 150. Accordingly, the plurality of biasing rails 120 may be configured to longitudinally span the at least one array of the arrays of magnets 104, 105, 150. In other words, at least one of the first array of magnets 104, the second array of magnets 106, and the third array of magnets 150 may be positioned longitudinally (e.g. in the direction of the x-axis of the coordinate axes of FIG. 1A) between the proximal point 130 and the distal point 132. In embodiments the plurality of biasing rails 120 may be arranged to bias the one or more arrays of magnets 104, 106, 150 against a blood vessel wall, as will be discussed in further detail with respect to FIGS. 3A and 3B.

In embodiments, the plurality of biasing rails 120 may extend radially from the non-active side 103 of the catheter 100. In other words, the proximal point 130 and distal point 132 may be positioned along the non-active side 103 of the catheter body 102. More particularly, in embodiments, a lateral center point 137 (FIG. 1B) of the plurality of biasing rails 120 may be diametrically opposite the active side 134 of the working site 135. The lateral center point 137 may be a point that is equidistant from the laterally outward (e.g. in the direction of the y-axis of the coordinate axes of FIG. 1A) biasing rails of the plurality of biasing rails 120 (i.e. the first biasing rails 122 and the second biasing rail 124). In embodiments, the working site 135 may be positioned longitudinally (e.g. in the direction of the x-axis of the coordinate axes of FIG. 1A) between the proximal point 130 and the distal point 132. In embodiments, the plurality of biasing rails 120 may be configured to bias the working site 135, and more specifically the active side 134 of the working site 135, against a blood vessel wall, as will be discussed in further detail with respect to FIGS. 3A and 3B.

In embodiments, the plurality of biasing rails 120 may be skewed proximally (e.g. skewed in the −x direction of the coordinate axes of FIG. 1A). In other words, a first distance L1 (in the direction of the x-axis of the coordinate axes of FIG. 1A) between the proximal point 130 and a vertex 131 of the plurality of biasing rails 120 may be less than a second distance L2 (in the direction of the x-axis of the coordinate axes of FIG. 1A) between the distal point 132 and the vertex 131 of the plurality of biasing rails 120. The vertex 131 of the plurality of biasing rails 120 may be the point longitudinally along (e.g. in the direction of the x-axis of the coordinate axes of FIG. 1A) the plurality of biasing rails 120 that exhibits a maximum height MH, or maximum radial deflection from, the catheter body 102, when the plurality of biasing rails are in an extended configuration. Therefore, in embodiments, the point of maximum height MH along the plurality of biasing rails 120 is closer to the proximal point 130 than the distal point 132 (e.g. in the direction of the x-axis of the coordinate axes of FIG. 1A). In such embodiments, the plurality of biasing rails 120 are particularly configured to bias the first array of magnets 104 and working site 135 against a wall of the blood vessel 300 (FIG. 3A).

Referring again to FIG. 1A in conjunction with FIG. 1B, which depicts the non-active side 103 of the catheter 100, the plurality of biasing rails 120 may include one or more connecting rails 126, 126', 126". The one or more connecting rails 126, 126', 126" may extend laterally between and join the first biasing rail 122 and the second biasing rail 124 of the plurality of biasing rails 120. The one or more connecting rails 126, 126', 126" may extend between the biasing rails 122 and 124 at points longitudinally between (e.g. in the direction of the x-axis of the coordinate axes of FIGS. 1A and 1B) the proximal point 130 and the distal point 132. The one or more connecting rails 126, 126', 126" may inhibit the first biasing rail 122 and the second biasing rail 124 from rotating away from or toward each other (i.e. rotating in opposite directions around the circumference of the catheter body 102) when contacting a wall of the blood vessel 300 (FIG. 3A).

As mentioned above, the plurality of biasing rails 120 may radially arch away from the catheter body 102 of the catheter 100 between the proximal point 130 and the distal point 132. In some embodiments the biasing rails 122, 124 of the plurality of biasing rails 120 may be fixedly secured to the catheter body 102 at the proximal point 130 and the distal point 132. In such embodiments, the biasing rails 122, 124 may be fixed to the catheter body 102 at the proximal point 130 and the distal point 132 with a suitable polymer or adhesive, such as glue, laser welding, heat shrunk plastic wrap, and the like. In embodiments, the proximal point 130 may be housed within a cap 142 coupled to the catheter body 102, and the distal point 132 may be housed within a cap 144 coupled to the catheter body 102. The caps 142, 144 may be metal, plastic, composite, or the like, and shield the proximal point 130 and the distal point 132 from the external environment.

In embodiments, the biasing rails 122, 124 of the plurality of biasing rails 120 may have a circular cross section. In embodiments, the biasing rails 122, 124 of the plurality of biasing rails 120 may be flat ribbons having a substantially rectangular cross section. In some embodiments, the biasing rails 122, 124 may transition between a first section of the biasing rails 122, 124 having a circular cross section and a second section of the biasing rails having a substantially rectangular cross section. For instance, a proximal end of the biasing rails 122, 124 adjacent to the proximal point 130 may have a circular cross section, a distal end of the biasing rails 122, 124 adjacent the distal point 132 may have a circular cross section, and a section of the biasing rails 122, 124 between the proximal and distal ends may have a rectangular cross section. In embodiments, the biasing rails 122, 124 of the plurality of biasing rails 120 may be made of metal, plastic, polymer, metal coated in plastic, a composite of any of said materials, and the like. For instance, the biasing rails 122, 124 may be nitinol, stainless steel, polyethylene terephthalate, polyether ether ketone, polytetrafluoroethylene, polyimide, and the like. The biasing rails 122, 124 may be a material that exhibits shape memory and returns to a set or desired shape. In embodiments, the one or more connecting rails 126, 126', 126" may be flat or round ribbons. The one or more connecting rails 126, 126', 126" may be metal, plastic, polymer, metal coated in plastic, a composite of any of said materials, and the like. The one or more connect rails 12, 126', 126" may be coupled to the biasing rails 122, 124 via any bonding techniques, e.g., adhesives, soldering, welding, or the like.

In some embodiments, the biasing rails 120 may expand from a low-profile configuration to an extended configuration, depicted in FIG. 1A. In the low-profile configuration, the plurality of biasing rails 120 may be positioned in a non-contacting state, in which the plurality of biasing rails 120 do not apply a biasing force to the wall of the blood vessel 300 (FIG. 3A) to bias the catheter 100 laterally within the blood vessel 300 (FIG. 3A). In the low-profile configuration, the plurality of biasing rails 120 may be maintained substantially flush with or within the catheter body 102 of the catheter 100. As such, the catheter 100 may be advanced to a desired location within the blood vessel 300 (FIG. 3A) without the plurality of biasing rails 120 extending radially from the catheter body 102 and applying a biasing force to the wall of the blood vessel 300 (FIG. 3A) to bias the catheter 100 laterally within the blood vessel 300 (FIG. 3A). In the extended configuration, at least a portion of the plurality of biasing rails 120 may radially extend outward from the outer surface of the catheter body 102 to be in a contacting state, in which at least a portion of the plurality of biasing rails 120 apply a biasing force to the wall of the blood vessel 300 (FIG. 3A). Accordingly, a maximum distance of radial deflection of the plurality of biasing rails 120 from the outer surface of the catheter body 102, when in the extended configuration, may be greater than the maximum distance of radial deflection of the plurality of biasing rails 120 from the outer surface of the catheter body 102, when in the low-profile configuration.

Figure 1C:
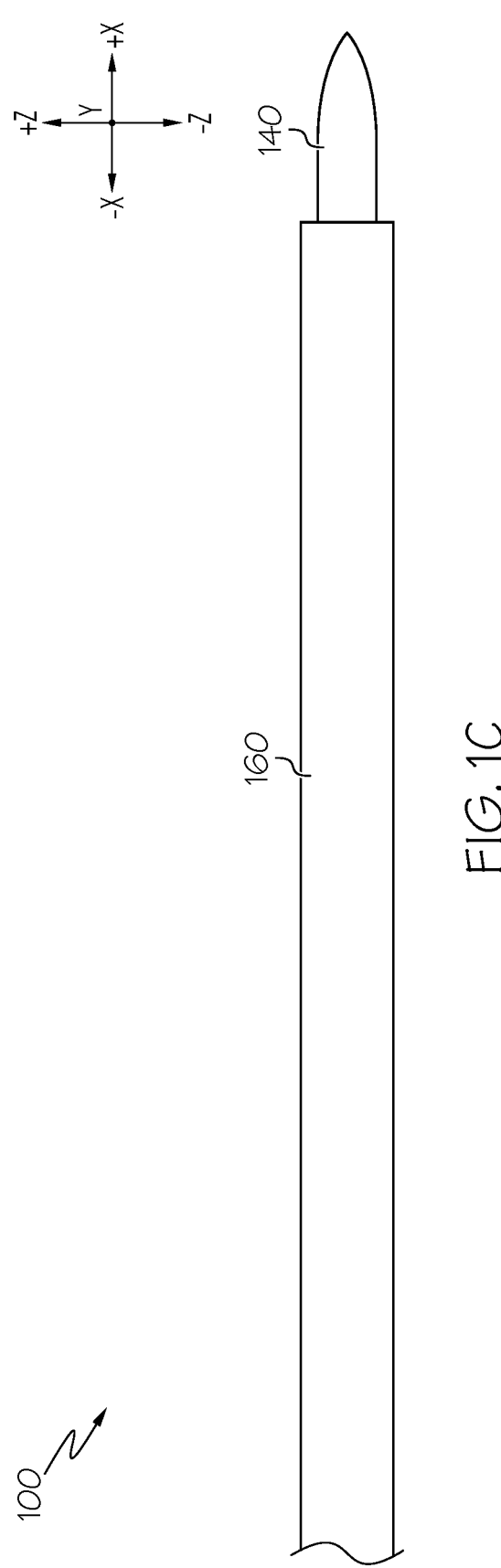
FIG. 1C schematically depicts a side view of a sheath distally advanced over the catheter of FIG. 1A, according to one or more embodiments shown and described herein.

In embodiments, the plurality of biasing rails 120 described herein may be biased toward the extended configuration. That is, the plurality of biasing rails 120 may be configured to self-expand from the low-profile configuration to the extended configuration. Put yet another way, the plurality of biasing rails 120 may be in their natural resting state in the extended configuration, with the biasing rails 122, 124 of the plurality of biasing rails 120 radially extending a predetermined distance away from the outer surface of the catheter body 102. In such embodiments, a force may be required to hold the plurality of biasing rails 120 in the low-profile configuration. For instance, referring to FIGS. 1A-1C, a sheath 160 may be advanced distally (e.g. in the +x direction of the coordinate axes of FIGS. 1A-1C) to maintain the plurality of biasing rails 120 in the low-profile configuration. The sheath 160 may include an inner lumen having a greater diameter than the catheter body 102 and the one or more arrays of magnets 104, 106, 150 of the catheter 100, thereby allowing the sheath 160 to be advanced distally over the catheter body 102 and one or more arrays of magnets 104, 106, 150, as depicted in FIG. 1C. Thus, with the sheath 160 advanced distally over the catheter body 102 and one or more arrays of magnets 104, 105, 150, the plurality of biasing rails 120 may be compressed by the sheath 160 against the catheter body 102. In other words, the plurality of biasing rails 120 may be compressed and maintained in the low-profile configuration within the space between the catheter body 102 and the sheath 160. The catheter 100 within the sheath 160 may be advanced within the blood vessel 300 (FIG. 3A) to a desirable location to form a fistula, for instance, at which point the sheath 160 may be retracted in the proximal direction (e.g. in the −x direction of the coordinate axes of FIGS. 1A-1C), thereby exposing the plurality of biasing rails 120. With the sheath 160 no longer applying a force to the plurality of biasing rails 120 to maintain the plurality of biasing rails 120 in the low-profile configuration, and due to the natural bias of the plurality of biasing rails 120, the plurality of biasing rails 120 may naturally expand into the extended configuration, as shown in FIG. 1A.

In some embodiments, the plurality of biasing rails 120 may be made of a shape-memory alloy, such as copper-aluminum-nickel and nickel-titanium, that changes shape due to environmental cues, such as temperature. For instance, the active shape of the plurality of biasing rails 120 may be the extended configuration depicted in FIG. 1A. The transition temperature of the shape-memory alloy may be above standard room temperatures. In some embodiments, the transition temperature of the shape-memory alloy may be roughly at internal body temperature. Therefore, outside of a patient, at standard room temperature, the plurality of biasing rails 120 may deform into the low-profile configuration, in which the plurality of biasing rails 120 are in a non-contacting state and do not extend radially away from the outer surface of the catheter body 102 to apply a biasing force to a wall of the blood vessel 300 (FIG. 3A). As the temperature of the plurality of biasing rails 120 increases, the plurality of biasing rails 120 may naturally transition from the low-profile configuration to the extended configuration, in which the plurality of biasing rails 120 are in a contacting state and extend radially away from the outer surface of the catheter body 102 to apply a biasing force to the wall of the blood vessel 300 (FIG. 3A) to bias the catheter 100 laterally within the blood vessel 300 (FIG. 3A). In embodiments, the plurality of biasing rails 120 may transition from the low-profile configuration to the extended configuration at temperatures above 30° C., temperatures above 32° C., temperatures above 35° C., and like temperatures between standard room temperature of 20° C. and internal body temperature at 37° C.

Figures 2A, 2B:
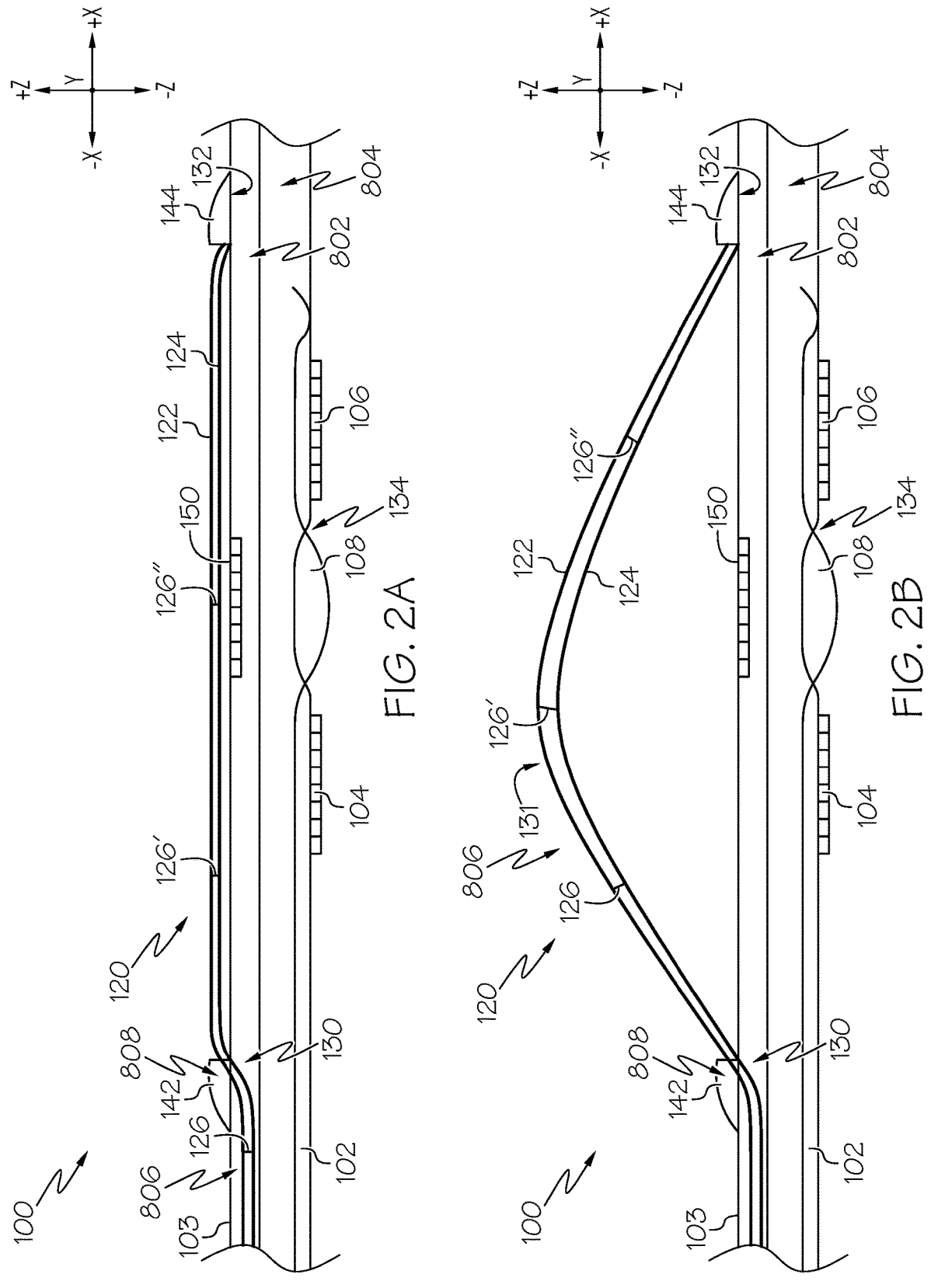
FIG. 2A schematically depicts a cross-sectional view of a catheter with a plurality of biasing rails in a low-profile delivery configuration, according to one or more embodiments shown and described herein.
FIG. 2B schematically depicts a cross-sectional view of the catheter of FIG. 2A with the plurality of biasing rails in an extended configuration, according to one or more embodiments shown and described herein.

In some embodiments, the plurality of biasing rails 120 described herein may be configured such that the plurality of biasing rails 120 are moveable within the catheter body 102 of the catheter 100. For instance, and with reference to FIGS. 2A and 2B, which depict sectional views of the interior of the catheter 100, the plurality of biasing rails 120 may extend through a lumen 802 of the catheter body 102. While the plurality of biasing rails 120 are depicted as extending through the lumen 802 and the electrode 108 is depicted as extending through a lumen 804 of the catheter body 102, it should be appreciated that in some embodiments, the plurality of biasing rails 120 and the electrode 108 may extend through a shared lumen, such as lumen 804. Physical interference between the movement of the plurality of biasing rails 120 in the catheter body 102 and the electrode 108 may be reduced when the plurality of biasing rails 120 extend through the lumen 802 and the electrode 108 extends though the lumen 804. In embodiments, the plurality of biasing rails 120 may extend through an opening 808 of the catheter body 102 at the proximal point 130. That is, the proximal point 130 may define the opening 808 into the lumen 802 of the catheter body 102. The plurality of biasing rails 120 may extend proximally (e.g. in the −x direction of the coordinate axes of FIGS. 2A and 2B) through the interior of the catheter body 102 through the lumen 802. Accordingly, the plurality of biasing rails 120 may be movable within the lumen 802 of the catheter body 102. In the low-profile configuration, as depicted in FIG. 2A, a proximal portion 806 of the plurality of biasing rails 120 may be housed within the lumen 802. The plurality of biasing rails 120 may move within the lumen 802 such that the proximal portion 806 of the plurality of biasing rails 120 expands outward from the opening 808. As the proximal portion 806 expands outward from the opening 808, the plurality of biasing rails 120 may radially extend away from the catheter body 102 between the proximal point 130 and the distal point 132 and move into the extended configuration as depicted in FIG. 2B.

In embodiments, the plurality of biasing rails 120 may be biased to the extended configuration. In other words, the proximal portion 806 of the plurality of biasing rails may be biased to expand outwardly from the opening 808. The sheath 160 (FIGS. 1A-1C) may maintain the plurality of biasing rails 120 in the low-profile configuration. For instance, the sheath 160 (FIGS. 1A-1C) may be advanced distally (e.g. in the +x direction of the coordinate axes of FIGS. 2A and 2B) over the catheter 100. The sheath 160 (FIGS. 1A-1C) may apply an inward force on the plurality of biasing rails 120, compressing the plurality of biasing rails 120 such that the proximal portion 806 of the plurality of biasing rails 120 slides proximally (e.g. in the −x direction of the coordinate axes of FIGS. 2A and 2B) within the lumen 802. The sheath 160 (FIGS. 1A-1C) may further prevent the proximal portion 806 from expanding outwardly from the opening 808. Accordingly, the proximal portion 806 may be maintained within the lumen 802, and the plurality of biasing rails 120 may be maintained in the low-profile configuration. Moreover, removal of the sheath 160 (FIGS. 1A-1C) proximally (e.g. in the −x direction of the coordinate axes of FIGS. 2A and 2B) may allow the proximal portion 806 of the plurality of biasing rails 120 to expand from the opening 808 due to the natural bias of the proximal portion 806. Accordingly, the plurality of biasing rails 120 may assume the extended configuration depicted in FIG. 2B.

It should be appreciated that, in embodiments, the plurality of biasing rails 120 may be fixed to the catheter body 102 at the distal point 132 and extend through the catheter body 102 and into the lumen 802 at the proximal point 130. In other embodiments, the plurality of biasing rails 120 may similarly be fixed to the catheter body 102 at the proximal point 130 and extend through the catheter body 102 and into the lumen 802 at the distal point 132. Therefore, the distal point 132 may define an access opening into the lumen 802. In such embodiments, the plurality of biasing rails 120 may operate as described above, in that the plurality of biasing rails 120 may transition between the low-profile configuration and the extended configuration depending on the expansion or compression of the plurality of biasing rails 120 through an opening at the distal point 132 in the catheter body 102. In some embodiments, the plurality of biasing rails 120 may extend through the catheter body 102 and into the lumen 802 at both the proximal point 130 and the distal point 132. In such embodiments, both the proximal portion 806 and a counterpart distal portion of the plurality of biasing rails 120 may be movable within the lumen 802.

In the embodiments so far discussed with reference to FIGS. 1A-2B, the natural bias of the plurality of biasing rails 120 may eliminate the need for a user-actuated control that in a first state holds the plurality of biasing rails 120 in a low-profile configuration for delivery through the vasculature and in a second state allows the plurality of biasing rails 120 to enter the extended configuration for applying a biasing force to the wall of the blood vessel 300 (FIG. 3A). Although the plurality of biasing rails 120 may be moveable between low-profile and extended configurations, this movement may occur as a natural result of the bias of the plurality of biasing rails 120 in combination with external forces (such as from the sheath 160 (FIG. 2A) or an inner wall of the lumen 802), and the plurality of biasing rails 120 remain in a single state throughout use. That is, during both advancement of the catheter 100 through vasculature and tissue ablation, the catheter 100 is in a state in which the plurality of biasing rails 120 would be able to be in the extended configuration in the absence of an external force pressing on the plurality of biasing rails 120. Due to the shape-memory of the plurality of biasing rails 120 and the natural bias of the plurality of biasing rails 120, the plurality of biasing rails 120 may return to a set shape (e.g. the extended configuration). Accordingly, the angle, shape, curvature, and distance of radial extension from the catheter body 102 of the plurality of biasing rails 120 in the extended configuration may be particularly selected. The distance of radial extension from the catheter body 102 of the plurality of biasing rails 120 may be particularly selected and/or configured based on the size of the catheter 100 and the size of the blood vessel 300 (FIG. 3A) the catheter 100 is advanced through. For instance, the distance of radial extension of the plurality of biasing rails 120 may be selected to bias the catheter 100 against a blood vessel wall in a blood vessel having a diameter of about 2 mm to about 4 mm, greater than 4 mm, greater than 6 mm, greater than 8 mm, about 10 mm, and the like.

Still referring to FIGS. 2A and 2B, in some embodiments, the plurality of biasing rails 120 may be user-manipulated from the low-profile configuration to the extended configuration. For example, in embodiments in which the plurality of biasing rails 120 extend proximally (e.g. in the −x direction of the coordinate axes of FIGS. 2A and 2B) through the lumen 802, the plurality of biasing rails 120 may extend to a hand control, switch, actuator, or other user-manipulated device coupled to the plurality of biasing rails 120. Through actuation of the user-manipulated device, a user may advance the plurality of biasing rails 120 distally (e.g. in the +x direction of the coordinate axes of FIGS. 2A and 2B) through the lumen 802 and/or retract the plurality of biasing rails 120 proximally (e.g. in the direction of the −x direction of the of the coordinate axes of FIGS. 2A and 2B) through the lumen. For instance, in some embodiments, the plurality of biasing rails 120 may be fixed to the catheter body 102 at the distal point 132. A user may advance the plurality of biasing rails 120, and particularly the proximal portion 806 of the plurality of biasing rails 120 distally (e.g. in the +x direction of the coordinate axes of FIGS. 2A and 2B) such that the proximal portion 806 of the plurality of biasing rails 120 expands outwardly from the opening 808. Accordingly, the plurality of biasing rails 120 may transition from the low-profile configuration depicted in FIG. 2A to the extended configuration depicted in FIG. 2B. In embodiments, the plurality of biasing rails 120 may be configured such that the plurality of biasing rails 120 assume a desired shape in the extended configuration following the expansion of the biasing rails 120 from the opening 808. In embodiments, the height (e.g. in the +z direction of the coordinate axes of FIGS. 2A and 2B) of the vertex 131 of the plurality of biasing rails 120 in the extended configuration may be determined by the amount of distal advancement (e.g. in the +x direction of the coordinate axes of FIGS. 2A and 2B) of the plurality of biasing rails 120 through the lumen 802. In other words, the further a user advances the plurality of biasing rails 120 through the lumen 802, the further the plurality of biasing rails 120 may extend radially from the outer surface of the catheter body 102.

In other embodiments, the distal point 132 of the plurality of biasing rails 120 may also be movable within the lumen 802. In other words, the plurality of biasing rails 120 may be entirely housed within the lumen 802 proximally (e.g. in the −x direction of the coordinate axes of FIGS. 2A and 2B) to the opening 808. A user may advance the plurality of biasing rails 120 such that the plurality of biasing rails 120 extend from the opening 808. The user may continue to advance the plurality of biasing rails 120 distally (e.g. in the +x direction of the coordinate axes of FIGS. 2A and 2B) until the plurality of biasing rails 120 contact the catheter body 102 beneath the cap 144. The plurality of biasing rails 120 may be shaped such that a distal portion of the plurality of biasing rails 120 is encouraged toward the cap 144 upon distal advancement (e.g. in the +x direction of the coordinate axes of FIGS. 2A and 2B) of the distal portion of the plurality of biasing rails 120. The plurality of biasing rails 120 may then be selectively manipulated, as discussed above, to control the radial extension of the plurality of biasing rails 120 from the catheter body 102.

Referring now to FIGS. 3A and 3B a system and method for forming a fistula between the first blood vessel 300 and a second blood vessel 302 with the first catheter 100 and the second catheter 400 will now be discussed. Referring first to FIG. 3A, the first catheter 100 may be advanced within a lumen of the blood vessel 300. The second catheter 400 may be placed in a blood vessel 302 that is adjacent to the blood vessel 300. The second catheter 400 may resemble the first catheter 100 discussed herein. In some embodiments, the second catheter 400 may not include an electrode 108. The second catheter 400 includes a catheter body 402. The catheter body 402 further defines a working site 435 having an active side 434. The second catheter 400 further includes a non-active side 403 defined by the catheter body 402 and the working site 435. Specifically, the active side 434 of the working site 435 may include a recess 408 configured to receive the electrode 108 of the first catheter 100. The recess 408 may be particularly shaped, sized, and/or the like to receive the electrode 108 of the first catheter 100 therein. In other embodiments, the second catheter 400 may include an electrode that extends from the working site 435 and radially away from the catheter body 402. The second catheter body 402 of the second catheter 400 may further include one or more arrays of magnets. For instance, the second catheter 400 may include a first array of magnets 404 positioned proximal (e.g. in the −x direction of the coordinate axes of FIGS. 3A and 3B) to the working site 435, a second array of magnets 406 positioned distal (e.g. in the +x direction of the coordinate axes of FIGS. 3A and 3B) to the working site 435, and/or a third array of magnets 450 positioned along the working site 435, and particularly along the non-active side 403 of the working site 435 in some embodiments. In embodiments, the second catheter 400 may include a second plurality of biasing rails 420 that mirror the first plurality of biasing rails 120 of the first catheter 100 in structure and operation. While in embodiments described below, the first catheter 100 includes the first plurality of biasing rails 120 and the second catheter 400 includes the second plurality of biasing rails 420, it should be appreciated that only one of the first catheter 100 and the second catheter 400 may include biasing rails.

The one or more arrays of magnets 104, 106, 150 of the first catheter 100 and the one or more arrays of magnets 404, 406, 450 of the second catheter 400 may be configured to promote rotational and axial alignment of the catheters 100 and 400. Proper axial and rotational alignment between catheters 100 and 400 may facilitate alignment of one or more fistula-forming elements, such as the working sites 135, 435 of the first and second catheters 100, 400, respectively. More specifically, proper axial and rotational alignment between the first catheter 100 and the second catheter 400 may facilitate alignment of the electrode 108 with the recess 408. The one or more arrays of magnets 104, 106, 150 of the first catheter 100 may be arranged such that the magnetic fields generated by the one or more arrays of magnets 104, 106, 150 are stronger in the direction of the active side 134 of the working site 135 (e.g. in the −z direction of the coordinate axes of FIGS. 3A and 3B) than in the direction of the non-active side 103 of the working site 135 (e.g. in the +z direction of the coordinate axes of FIGS. 3A and 3B). Similarly, the one or more arrays of magnets 404, 406, 450 of the second catheter 400 may be arranged such that the magnetic fields generated by the one or more arrays of magnets 404, 406, 450 are stronger in the direction of the active side 434 of the working site 435 (e.g. in the +z direction of the coordinate axes of FIGS. 3A and 3B) than in the direction of the non-active side 403 of the working site 435 (e.g. in the −z direction of the coordinate axes of FIGS. 3A and 3B). In such embodiments, the strength of the magnetic fields in the directions of the active sides 134, 434 of the working sites 135, 435, respectively, may promote rotational alignment between the active side 134 of the working site 135 of first catheter 100 in the first blood vessel 300 and the active side 434 of the working site 435 of the second catheter 400 in the second blood vessel 302.

The catheters 100 and 400, as depicted in FIG. 3A are axially misaligned, such that the electrode 108 of the first catheter 100 is not aligned with the recess 408 of the second catheter 400 in the x-direction of the coordinate axes of FIGS. 3A and 3B. Moreover, as depicted in FIG. 3A, for instance, the first catheter 100 and the second catheter 400 are in weak coaptation. When in weak coaptation, space may remain between at least one of the active side 134 of the working site 135 of the first catheter 100 and an adjacent wall of the blood vessel 300 and the active side 434 of the working site 435 of the second catheter 400 and an adjacent wall of the blood vessel 302. Therefore, in weak coaptation, the active side 134 of the working site 135 and the active side 434 of the working site 435 are not in close approximation with one another (e.g. in the direction of the z-axis of the coordinate axes of FIGS. 3A and 3B).

Each array of magnets 404, 406, 450 of the second catheter 400 may be configured to mate with a corresponding array of magnets 104, 106, 150 of the first catheter 100, and vice versa, such that the first catheter 100 and the second catheter 400 may be aligned and coapted. As used herein, the terms "coapted" and/or "strong coaptation" may be understood to mean that the first catheter 100 and the second catheter 400 are in close approximation (e.g. in the direction of the z-axis of the coordinate axes of FIGS. 3A and 3B) such that the electrode 108 of the first catheter 100 may enter the recess 408 of the second catheter 400. As used herein, the term "mate" may be understood to mean a mutual attraction between an array of magnets of the first catheter 100 and an array of magnets of the second catheter 400. For instance, the first array of magnets 104 positioned proximal (e.g. in the −x direction of the coordinate axes of FIGS. 3A and 3B) the working site 135 of the catheter 100 may be configured to mate with the first array of magnets 404 positioned proximal (e.g. in the −x direction of the coordinate axes of FIGS. 3A and 3B) the working site 435 of the second catheter 400. The second array of magnets 106 positioned distal (e.g. in the +x direction of the coordinate axes of FIGS. 3A and 3B) the working site 135 of the catheter 100 may be configured to mate with the second array of magnets 406 positioned distal (e.g. in the +x direction of the coordinate axes of FIGS. 3A and 3B) the working site 435 of the second catheter 400. Similarly, the third array of magnets 150 positioned along the non-active side 103 of the working site 135 of the first catheter 100 may be configured to mate with the third array of magnets 450 positioned along the non-active side 403 of the working site 435 of the second catheter 400. It should be appreciated that the third array of magnets 150 of the first catheter 100 and the third array of magnets 450 of the second catheter 400 may be configured and arranged such that when mated, coaptation is promoted between the active side 134 of the working site 135 and the active side 434 of the working site 435 such that the third array of magnets 150 and the third array of magnets 450 remain separated by the working sites 135, 435 (e.g. in the direction of the z-axis of the coordinate axes of FIGS. 3A and 3B).

During a fistula-forming procedure, however, the one or more arrays of magnets 104, 106, and 150 of the first catheter 100 and the one or more arrays of magnets 404, 406, and 450 of the second catheter 400 may be insufficient on their own to align and coapt the first catheter 100 and the second catheter 400. For instance, due to limitations in the strength of the one or more arrays of magnets 104, 106, 150 of the first catheter 100 and the one or more arrays of magnets 404, 406, 450 of the second catheter 400, limitations on the degree of flexibility of the first catheter 100 and the second catheter 400, a distance between the vessels 300 and 302, and/or a tortuous anatomy of the first blood vessel 300 and/or the second blood vessel 302, the one or more arrays of magnets 104, 106, 150 of the first catheter 100 and the one or more arrays of magnets 404, 406, 450 of the second catheter 400 may be unable to mate. Therefore, as depicted in FIG. 3A the first catheter 100 and the second catheter 400 may be axially misaligned and/or in weak coaptation.

The plurality of biasing rails 120 of the first catheter 100 and/or the plurality of biasing rails 420 of the second catheter 400 may assist the one or more arrays of magnets 104, 106, 150 of the first catheter 100 and the one or more arrays of magnets 404, 406, 450 of the second catheter 400 in aligning and coapting the first catheter 100 and the second catheter 400. For instance, referring to FIG. 3A, the first catheter 100 and the second catheter 400 may be advanced in the blood vessels 300 and 302, respectively, with the plurality of biasing rails 120 and/or the plurality of biasing rails 420 in the low-profile configuration to ease distal advancement (e.g. in the +x direction of the coordinate axes of FIGS. 3A and 3B) of the catheters 100 and 400. The plurality of biasing rails 120 of the first catheter 100 and/or the plurality of biasing rails 420 of the second catheter 400 may be maintained in the low-profile configurations by any of the methods discussed above with respect to FIGS. 1A-2B, for instance. With the plurality of biasing rails 120 of the first catheter 100 and/or the plurality of biasing rails 420 of the second catheter 400 in the low-profile configuration, the first catheter 100 and the second catheter 400 may be advanced within the blood vessels 300 and 302, respectively, until the working site 135 of the first catheter 100 and the working site 435 of the second catheter 400 are generally positioned at a desired site for forming a fistula between the blood vessels 300 and 302. However, as stated above and depicted in FIG. 3A, the one or more arrays of magnets 104, 106, 150 of the first catheter 100 and the one or more arrays of magnets 404, 406, 450 of the second catheter may be unable to align and coapt the catheters 100 and 400 on their own.

Referring now to FIG. 3B, to encourage alignment and coaptation between the first catheter 100 and the second catheter 400, the plurality of biasing rails 120 of the first catheter 100 and/or the plurality of biasing rails 420 of the second catheter 400 may be transitioned from the low-profile configuration to the extended configuration. In some embodiments, only the plurality of biasing rails 120 of the first catheter 100 may be transitioned from the low-profile configuration to the extended configuration to encourage alignment and coaptation between the first catheter 100 and the second catheter 400. In some embodiments, only the plurality of biasing rails 420 of the second catheter 400 may be transitioned from the low-profile configuration to the extended configuration to encourage alignment and coaptation between the first catheter 100 and the second catheter 400. In embodiments, the plurality of biasing rails 120 and/or the plurality biasing rails 420 may transition from the low-profile configuration to the extended configuration by any device or method discussed with reference to FIGS. 1A-2B.

In embodiments in which the plurality of biasing rails 120 and 420 are naturally biased from the low-profile configuration to the extended configuration, the plurality of biasing rails 120 and 420 may begin to extend radially away from the catheter bodies 102 and 402, respectively. For instance, the plurality of biasing rails 120 may extend toward the maximum height MH (FIG. 1A) of the extended configuration until the plurality of biasing rails 120 contact a wall of the blood vessel 300. Accordingly, the plurality of biasing rails 120 may apply a biasing force against the wall of the blood vessel 300, resulting in a biasing reaction force to be applied to the catheter 100 to push the active side 134 and/or the one or more magnetic arrays against a wall of the blood vessel 300. More specifically, as the lateral center point 137 (FIG. 1B) of plurality of biasing rails 120 is diametrically opposite the active side 134 of the working site 135, the biasing reaction force may direct the active side 134 of the working site 135 against a wall of the blood vessel 300 at a position diametrically opposite the lateral center point 137 (FIG. 1B) of the plurality of biasing rails 120.

Similarly, the plurality of biasing rails 420 of the second catheter 400 may transition to the extended configuration to contact a wall of the second blood vessel 302, resulting in a biasing reaction force that directs the active side 434 of the working site 435 of the second catheter 400 against a wall of the second blood vessel 302. For example, the biasing rails 420 of the second catheter 400 may be deployed when the active side 434 of the working site 435 of the second catheter 400 is substantially aligned with the active side 134 of the working site 135 of the first catheter 100. Accordingly, the plurality of biasing rails 120 and 420 may strengthen the coaptation between the first catheter 100 and the second catheter 400. For example, and as described above, the plurality of biasing rails 120 of the first catheter 100, in addition to the active side 134 of the working site 135, bias the one or more arrays of magnets 104, 106, 150 against the wall of the first blood vessel 300, and the biasing rails 420 of the second catheter 400, in addition to the active side 434 of the working site 435, bias the one or more arrays of magnets 404, 406, 450 against the wall of the second blood vessel 302 thereby increasing attraction between the one or more arrays of magnets 104, 105, 150 of the first catheter with the one or more arrays of magnets 404, 406, 450 by decreasing distance between them. For example, once in closer approximation, the one or more arrays of magnets 104, 106, 150 of the first catheter 100 and the one or more arrays of magnets 404, 406, 450 of the second catheter 400 may be able to mate, overcoming any previous barriers, such as the distance between magnets, the flexibility of the catheters 100, 400, the distance between the vessels 300, 302, the tortuous anatomy of the first and second blood vessels 300, 302, and/or the like. The mating of the one or more arrays of magnets 104, 106, 150 of the first catheter 100 and the one or more arrays of magnets 404, 406, 450 of the second catheter 400 may coapt and align the catheters 100 and 400. After the first catheter 100 and the second catheter 400 are coapted and aligned, the electrode 108 may be advanced and energized to ablate the wall of the first blood vessel 300 and the wall of the second blood vessel 302 and advance into the recess 408 of the second catheter 400, thereby forming a fistula between the first and second blood vessels 300, 302.

Referring now to FIG. 4, a side view of a catheter 200 is depicted. The catheter 200 may resemble the catheter 100 discussed in FIGS. 1A-3B in all aspects except as discussed herein. For instance, similar to the catheter 100, the catheter 200 may include the catheter body 102 defining the working site 135 and the one or more arrays of magnets 104, 106, 150. The working site 135 may include the active side 134 diametrically opposite the non-active side 103. The catheter 200 includes the plurality of biasing rails 120 that may radially arch away from the catheter body 102 between the proximal point 130 and the distal point 132. Unlike the catheter 100 discussed above, the distal point 132 of the catheter 200 may be positioned along the non-active side 103 of the working site 135. In such embodiments, the first array of magnets 104 may be positioned between the proximal point 130 and the distal point 132. In embodiments, the distal point 132 may be longitudinally positioned (e.g. in the direction of the x-axis of the coordinate axes of FIG. 4) along the third array of magnets 150. In embodiments, the location of the distal point 132 and/or the positioning and/or length of the third array of magnets 150 may be adjusted such that the third array of magnets 150 is positioned between (e.g. in the direction of the x-axis of the coordinate axes of FIG. 4) the proximal point 130 and the distal point 132. In some embodiments, the proximal point 130 may be positioned along the non-active side 103 of the working site 135 and the distal point 132 may be at a proximal end (e.g. in the −x direction of the coordinate axes of FIG. 4) of the distal tip 140 such that the second array of magnets 106 is positioned between the proximal point 130 and the distal point 132. In such embodiments, the third array of magnets 150 may be positioned between the proximal point 130 and the distal point 132. Similar to the catheter 100, the plurality of biasing rails 120 of the catheter 200 may be coupled to, or movable within a lumen of, the catheter body 102 at the proximal point 130, and the plurality of biasing rails 120 may be coupled to, or movable within a lumen of, the catheter body 102 at the distal point 132.

Referring now to FIG. 5, a side view of a catheter 500 is depicted. The catheter 500 may resemble the catheter 100 discussed in FIGS. 1A-3B in all aspects except as discussed herein. For instance, similar to the catheter 100, the catheter 500 may include the catheter body 102 defining the working site 135 and the one or more arrays of magnets 104, 106, 150. The working site 135 may include the active side 134 diametrically opposite the non-active side 103. The catheter 500 includes the plurality of biasing rails 120. Unlike the catheter 100, the plurality of biasing rails 120 of the catheter 500 may define a first arch 510 and a second arch 520. The first arch 510 may radially extend away from catheter body 102 between the proximal point 130 and an intermediate point 530. The second arch 520 may radially extend away from the catheter body 102 between the intermediate point 530 and the distal point 132. In embodiments, intermediate point 530 may be along or within the non-active side 103 of the working site 135. In embodiments, the first plurality of magnets 104 may be positioned between (e.g. in the direction of the x-axis of the coordinate axes of FIG. 5) the proximal point 130 and the intermediate point 530. In some embodiments, the third array of magnets 150 may be positioned between (e.g. in the direction of the x-axis of the coordinate axes of FIG. 5) the proximal point 130 and the intermediate point 530. In some embodiments, the intermediate point 530 may be positioned longitudinally along (e.g. in the direction of the x-axis of the coordinate axes of FIG. 5) the third array of magnets 150. In embodiments, the third array of magnets 150 may be positioned between (e.g. in the direction of the x-axis of the coordinate axes of FIG. 5) the intermediate point 530 and the distal point 132. In embodiments, the second array of magnets 106 may be positioned between the intermediate point 530 and the distal point 132. Similar to the catheter 100, the plurality of biasing rails 120 of the catheter 500 may be coupled to, or movable within a lumen of, the catheter body 102 at the proximal point 130, and the plurality of biasing rails 120 may be coupled to, or movable within a lumen of, the catheter body 102 at the distal point 132. In embodiments, the plurality of biasing rails 120 may be coupled to the non-active side 103 of the working site 135 at the intermediate point 530. In embodiments, the plurality of biasing rails 120 may pass through a lumen of the catheter 500 at the intermediate point 530. In such embodiments, the plurality of biasing rails 120 may be movable within the lumen of the catheter 500 at the intermediate point 530.

Referring now to FIG. 6, a side view of a catheter 600 is depicted. The catheter 600 may resemble the catheter 100 discussed in FIGS. 1A-3B in all aspects except as discussed herein. For instance, similar to the catheter 100, the catheter 600 may include the catheter body 102 defining the working site 135 and the one or more arrays of magnets 104, 106, 150. The working site 135 may include the active side 134 diametrically opposite the non-active side 103. The catheter 600 includes the plurality of biasing rails 120. Unlike the catheter 100, the plurality of biasing rails 120 of the catheter 600 may define a first biasing rail in the form of a first loop 610 and a second basing rail in the form of a second loop 620. The first loop 610 may extend from the proximal point 130 in the distal direction (e.g. in the +x direction of the coordinate axes of FIG. 6). The second loop 620 may extend from the distal point 132 in the proximal direction (e.g. in the −x direction of the coordinate axes of FIG. 6). The first loop 610 is defined by a strip of biasing rail material that extends from the catheter body 102 at the proximal point 130 and returns to the catheter body 102 at the proximal point 130. The second loop 620 is defined by a strip of biasing rail material that extends from the catheter body 102 at the distal point 132 and returns to the catheter body 102 at the distal point 132. The first loop 610 may intertwine with the second loop 620 at an intersection point 630. Therefore, a portion of the first loop 610 may be within the second loop 620, and a portion of the second loop 620 may be within the first loop 610. One or more connecting rails 126 may extend laterally between the first loop 610 at a point longitudinally (e.g. in the direction of the x-axis of the coordinate axes of FIG. 6) between the proximal point 130 and the intersection point 630. One or more connecting rails 126' may extend laterally between the second loop 620 at a point longitudinally between the intersection point 630 and the distal point 132. Similar to the catheter 100, the plurality of biasing rails 120 of the catheter 600 may be coupled to, or movable within a lumen of, the catheter body 102 at the proximal point 130, and the plurality of biasing rails 120 may be coupled to, or movable within a lumen of, the catheter body 102 at the distal point 132.

Referring now to FIG. 7 a side view of a catheter 700 is depicted. The catheter 700 may resemble the catheter 100 discussed in FIGS. 1A-3B in all aspects except as discussed herein. For instance, similar to the catheter 100, the catheter 700 may include the catheter body 102 defining the working site 135 and the one or more arrays of magnets 104, 106, 150. The working site 135 may include the active side 134 diametrically opposite the non-active side 103. The catheter 700 includes the plurality of biasing rails 120. Unlike the catheter 100, the plurality of biasing rails 120 of the catheter 700 may define a substantially helical structure that wraps circumferentially around the catheter body 102 between the proximal point 130 and the distal point 132. It should be appreciated that in some embodiments the catheter 700 may include a single biasing rail, such as the biasing rail 122 or 124, as a helix around the catheter body 102. The plurality of biasing rails 120 may extend radially away from the catheter body 102 at the proximal point 130 and the distal point 132. The plurality of biasing rails 120 may have any desirable amplitude. The plurality of biasing rails 120 may have any desirable pitch. In embodiments, any or all of the one or more arrays of magnets 104, 106, 150 may be between (e.g. in the direction of the x-axis of the coordinate axes of FIG. 7) the proximal point 130 and the distal point 132. Similar to the catheter 100, the plurality of biasing rails 120 of the catheter 700 may be coupled to, or movable within a lumen of, the catheter body 102 at the proximal point 130, and the plurality of biasing rails 120 may be coupled to, or movable within a lumen of, the catheter body 102 at the distal point 132.

In some embodiments, the plurality of biasing rails 120 may be arranged such that a first distance H1 between the catheter body 102 and a vertex 131 of the plurality of biasing rails 120 that is diametrically opposite the active side 134 of the working site 135 is substantially equal to a second distance H2 between the catheter body 102 and a vertex 702 of the plurality of biasing rails 120 that is diametrically opposite the non-active side 103 of the working site 135. In other embodiments, the second distance H2 between the catheter body 102 and the vertex 702 of the plurality of biasing rails 120 that is diametrically opposite the non-active side 103 of the working site 135 may be minimized. In such embodiments, the vertex 702 of the plurality of biasing rails 120, may abut the catheter body 102. Therefore, the plurality of biasing rails 120 may not extend radially from the catheter body 102 diametrically opposite from the non-active side 103 of the working site 135. In such embodiments, the vertex 131 of the plurality of biasing rails 120 may extend radially from the catheter body diametrically opposite from the active side 134 of the working site 135 any desirable first distance H1. In such embodiments, the vertex 131 of the plurality of biasing rails 120 may contact a wall of the blood vessel 300 (FIG. 3A) at a point diametrically opposite the active side 134 of the working site 135. Therefore, the plurality of biasing rails 120 may bias the active side 134 of the working site 135 against a wall of the blood vessel 300 (FIG. 3A) that is diametrically opposite the point of contact between the vertex 131 of the plurality of biasing rails 120 and the wall of the blood vessel 300 (FIG. 3A). In embodiments, the plurality of biasing rails 120 may be fixed to the catheter body 102 at the proximal point 130 and the distal point 132. In such embodiments, as the plurality of biasing rails 120 contact a wall of the blood vessel 300 (FIG. 3A) at a point diametrically opposite the active side 134 of the working site 135 (e.g. the vertex 131), opposite axial forces may be generated by the plurality of biasing rails 120 that buckle the catheter body 102 between the proximal point 130 and the distal point 132, causing the non-active side 103 of the catheter 700 to move to a position depicted by the dashed line 103'. Accordingly, the working site 135 and the one or more arrays of magnets 104, 106, 150 may be biased against a wall of the blood vessel 300 (FIG. 3A) that is diametrically opposite the point of contact between the vertex 131 of the plurality of biasing rails 120 and the wall of the blood vessel 300 (FIG. 3A).

Embodiments can be described with reference to the following numerical clause:

1. A system for forming a fistula between two blood vessels, comprising: a first catheter comprising a first catheter body, an electrode, one or more arrays of magnets, and a first plurality of biasing rails, wherein: the electrode is configured to project from a working site of the first catheter and define an active side of the first catheter; the one or more arrays of magnets are arranged longitudinally along the first catheter body; the first plurality of biasing rails longitudinally extend along a length of the first catheter body and are configured to radially arch away from the first catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets; the first plurality of biasing rails extend from a non-active side of the first catheter body such that the first plurality of biasing rails are configured to bias the working site and the one or more arrays of magnets against a first blood vessel wall; and the first plurality of biasing rails are joined by a connecting rail that laterally extends between the first plurality of biasing rails at a point between the proximal point and the distal point.

2. The system of clause 1, wherein the working site is longitudinally positioned between the proximal point and the distal point.

3. The system of any preceding clause, wherein the distal point is positioned on the non-active side of the working site.

4. The system of any preceding clause, wherein the first plurality of biasing rails comprises: a first loop extending from the proximal point in a distal direction; and a second loop extending from the distal point of in a proximal direction, wherein: the first loop and the second loop intertwine at an intersection point between the proximal point and the distal point.

5. The system of any preceding clause, wherein the first plurality of biasing rails couple to the first catheter body at an intermediate point between the proximal point and the distal point.

6. The system of any preceding clause, wherein the intermediate point is longitudinally positioned along the working site opposite the electrode.

7. The system of any preceding clause, wherein the first plurality of biasing rails define a helix extending circumferentially around the first catheter body between the proximal point and the distal point.

8. The system of any preceding clause, wherein the distal point is positioned proximal a distal tip of the first catheter body.

9. The system of any preceding clause, wherein the first plurality of biasing rails are rigidly coupled to the first catheter body at the distal point and the proximal point with an adhesive or a polymer.

10. The system of any preceding clause, wherein one of the proximal point and the distal point define an access opening into a lumen within the first catheter body, and the plurality of biasing rails are configured to slide within the lumen of the first catheter body between an extended position and a low-profile position.

11. The system of any preceding clause, wherein the first catheter further comprises a sleeve configured to be advanced distally to compress the first plurality of biasing rails against the first catheter body.

12. The system of any preceding clause, wherein the first plurality of biasing rails comprise nitinol, stainless steel, polyether ether ketone, polyethylene terephthalate, polyimide, or polytetrafluoroethylene.

13. The system of any preceding clause, wherein the first plurality of biasing rails comprise a circular cross section.

14. The system of any preceding clause, wherein the first plurality of biasing rails comprise substantially flat ribbons having a substantially rectangular cross section.

15. The system of any preceding clause, comprising a second catheter, wherein the first catheter is configured to be positioned within a first blood vessel and the second catheter is configured to be positioned within a second blood vessel adjacent to the first blood vessel.

16. The system of any preceding clause, wherein the second catheter further comprises a recessed region defining an active side of the second catheter, the recessed region configured to receive the electrode of the first catheter.

17. The system of any preceding clause, wherein the second catheter further comprises a second catheter body and one or more arrays of magnets arranged longitudinally along the second catheter body.

18. The system of any preceding clause, wherein the second catheter further comprises: a second plurality of biasing rails, wherein: the second plurality of biasing rails longitudinally extend along a length of the second catheter body and are configured to radially arch away from the second catheter body between a proximal point positioned proximal a first end of at least one array of the one or more arrays of magnets of the second catheter and a distal point positioned distal to a second end of the at least one array of the one or more arrays of magnets of the second catheter so as to longitudinally span the at least one array of the one or more arrays of magnets; the second plurality of biasing rails extend from a non-active side of the second catheter body such that the second plurality of biasing rails are configured to bias the recessed region and the one or more arrays of magnets of the second catheter against a second blood vessel wall; and the second plurality of biasing rails are joined by a connecting rail that laterally extends between the second plurality of biasing rails at a point between the proximal point and the distal point.

19. The system of any preceding clause, wherein the recessed region is longitudinally positioned between the proximal point and the distal point.

20. A method of forming a fistula between a first blood vessel and a second blood vessel, comprising: advancing a first catheter into the first blood vessel, wherein the first catheter comprises: a first catheter body, an electrode, one or more arrays of magnets, and a first plurality of biasing rails, wherein: the electrode is configured to project from a working site of the first catheter and define an active side of the first catheter; the one or more arrays of magnets are arranged longitudinally along the first catheter body; the first plurality of biasing rails longitudinally extend along a length of the first catheter body and are configured to radially arch away from the first catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets; and the first plurality of biasing rails extend from a non-active side of the first catheter body such that the first plurality of biasing rails are configured to bias the working site and the one or more arrays of magnets against a first blood vessel wall; and ablating tissue with the electrode to form the fistula.

21. The method of clause 20, wherein the working site is longitudinally positioned between the proximal point and the distal point.

22. The method of any preceding clause, further comprising: advancing a second catheter into the second blood vessel; and aligning the electrode of the first catheter with the second catheter.

23. The method of any preceding clause, wherein the second catheter comprises a recess, wherein aligning the electrode of the first catheter with the second catheter comprises aligning the electrode with the recess.

24. The method of any preceding clause, wherein: the second catheter further comprises a second catheter body and one or more arrays of magnets arranged longitudinally along the second catheter body; and the electrode of the first catheter is aligned with the second catheter via the one or more arrays of magnets of the first catheter and the one or more arrays of magnets of the second catheter.

25. The method of any preceding clause, wherein the second catheter further comprises: a second plurality of biasing rails, wherein: the second plurality of biasing rails longitudinally extend along a length of the second catheter body and are configured to radially arch away from the second catheter body between a proximal point positioned proximal a first end of at least one array of the one or more arrays of magnets of the second catheter and a distal point positioned distal to a second end of the at least one array of the one or more arrays of magnets of the second catheter so as to longitudinally span the at least one array of the one or more arrays of magnets; and the second plurality of biasing rails extend from a non-active side of the second catheter body such that the second plurality of biasing rails are configured to bias the recess and the one or more arrays of magnets of the second catheter against a second blood vessel wall.

26. The method of any preceding clause, wherein the recess is longitudinally positioned between the proximal point and the distal point.

27. A system for forming a fistula between two blood vessels, comprising: a first catheter comprising a catheter body, an electrode, one or more arrays of magnets, and a plurality of biasing rails, wherein: the electrode is configured to project from a working site of the first catheter and define an active side of the first catheter; the one or more arrays of magnets are arranged longitudinally along the catheter body; the plurality of biasing rails longitudinally extend along a length of the catheter body; the plurality of biasing rails are configured to radially arch away from the catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets; the plurality of biasing rails extend from a non-active side of the catheter body such that the plurality of biasing rails are configured to bias the working site and the one or more arrays of magnets against a first blood vessel wall; the plurality of biasing rails are joined by a connecting rail that laterally extends between the plurality of biasing rails at a point between the proximal point and the distal point; and the plurality of biasing rails comprise a proximal portion extending through a lumen of the catheter body, wherein: the proximal portion may be advanced in the lumen to transition the plurality of biasing rails to an extended configuration, wherein the plurality of biasing rails radially arch away from the catheter body; and the proximal portion may be retracted in the lumen to transition the plurality of biasing rails to a low-profile configuration, wherein a maximum distance of radial deflection of the plurality of biasing rails is less than a maximum distance of radial deflection of the plurality of biasing rails in the extended configuration.

28. The system of clause 27, wherein the plurality of biasing rails are naturally biased from the low-profile configuration to the extended configuration.

29. The system of any preceding clause, wherein the first catheter further comprises a sleeve configured to be advanced distally to maintain the plurality of biasing rails in the low-profile configuration.

30. The system of any preceding clause, wherein the plurality of biasing rails are substantially flush with or within the catheter body when in the low-profile configuration.

It should now be understood that embodiments of the present disclosure are directed to devices, systems, and methods for forming a fistula between two blood vessels. For example, a catheter may include a catheter body, an electrode, a first array of magnets, and a first plurality of biasing rails. The electrode is configured to project from a working site of the catheter. The first array of magnets are arranged longitudinally along the catheter body. The first plurality of biasing rails longitudinally extend along a length of the catheter body and are configured to radially arch away from the catheter body between a proximal point of the first plurality of biasing rails and a distal point of the first plurality of biasing rails. The first plurality of biasing rails are joined by a connecting rail that laterally extends between the first plurality of biasing rails at a point between the proximal point of the first plurality of biasing rails and the distal point of the first plurality of biasing rails. The first plurality of biasing rails longitudinally span the first array of magnets and extend from a non-active side of the catheter body, such that the first plurality of biasing rails are configured to bias the working site and the first array of magnets against a first blood vessel wall. Accordingly, the first plurality of biasing rails enhance the ability of the catheter to form a fistula.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A system for forming a fistula between two blood vessels, comprising:
   a first catheter comprising a first catheter body, an electrode, one or more arrays of magnets, and a first plurality of biasing rails, wherein:
   the electrode is configured to project from a working site of the first catheter and define an active side of the first catheter;
   the one or more arrays of magnets are arranged longitudinally along the first catheter body;
   the first plurality of biasing rails longitudinally extend along a length of the first catheter body and are configured to radially arch away from the first catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets;
   the first plurality of biasing rails extend from a non-active side of the first catheter body such that the first plurality of biasing rails are configured to bias the working site and the one or more arrays of magnets against a first blood vessel wall; and
   the first plurality of biasing rails are joined by a connecting rail that laterally extends between the first plurality of biasing rails at a point between the proximal point and the distal point.

2. The system of claim 1, wherein the working site is longitudinally positioned between the proximal point and the distal point.

3. The system of claim 1, wherein the distal point is positioned on the non-active side of the working site.

4. The system of claim 1, wherein the first plurality of biasing rails comprises:
   a first loop extending from the proximal point in a distal direction; and
   a second loop extending from the distal point of in a proximal direction, wherein:
   the first loop and the second loop intertwine at an intersection point between the proximal point and the distal point.

5. The system of claim 1, wherein the first plurality of biasing rails couple to the first catheter body at an intermediate point between the proximal point and the distal point.

6. The system of claim 5, wherein the intermediate point is longitudinally positioned along the working site opposite the electrode.

7. The system of claim 1, wherein the first plurality of biasing rails define a helix extending circumferentially around the first catheter body between the proximal point and the distal point.

8. The system of claim 1, wherein the distal point is positioned proximal a distal tip of the first catheter body.

9. The system of claim 8, wherein the first plurality of biasing rails are rigidly coupled to the first catheter body at the distal point and the proximal point with an adhesive or a polymer.

10. The system of claim 8, wherein one of the proximal point and the distal point define an access opening into a lumen within the first catheter body, and the plurality of biasing rails are configured to slide within the lumen of the first catheter body between an extended position and a low-profile position.

11. The system of claim 1, wherein the first catheter further comprises a sleeve configured to be advanced distally to compress the first plurality of biasing rails against the first catheter body.

12. The system of claim 1, wherein the first plurality of biasing rails comprise nitinol, stainless steel, polyether ether ketone, polyethylene terephthalate, polyimide, or polytetrafluoroethylene.

13. The system of claim 1, wherein the first plurality of biasing rails comprise a circular cross section.

14. The system of claim 1, wherein the first plurality of biasing rails comprise substantially flat ribbons having a substantially rectangular cross section.

15. The system of claim 1, further comprising a second catheter, wherein the first catheter is configured to be positioned within a first blood vessel and the second catheter is configured to be positioned within a second blood vessel adjacent to the first blood vessel.

16. The system of claim 15, wherein the second catheter further comprises a recessed region defining an active side of the second catheter, the recessed region configured to receive the electrode of the first catheter.

17. The system of claim 16, wherein the second catheter further comprises a second catheter body and one or more arrays of magnets arranged longitudinally along the second catheter body.

18. The system of claim 17, wherein the second catheter further comprises:

a second plurality of biasing rails, wherein:

the second plurality of biasing rails longitudinally extend along a length of the second catheter body and are configured to radially arch away from the second catheter body between a proximal point positioned proximal a first end of at least one array of the one or more arrays of magnets of the second catheter and a distal point positioned distal to a second end of the at least one array of the one or more arrays of magnets of the second catheter so as to longitudinally span the at least one array of the one or more arrays of magnets;

the second plurality of biasing rails extend from a non-active side of the second catheter body such that the second plurality of biasing rails are configured to bias the recessed region and the one or more arrays of magnets of the second catheter against a second blood vessel wall; and the second plurality of biasing rails are joined by a connecting rail that laterally extends between the second plurality of biasing rails at a point between the proximal point and the distal point.

19. The system of claim 18, wherein the recessed region is longitudinally positioned between the proximal point and the distal point.

20. A method of forming a fistula between a first blood vessel and a second blood vessel, comprising:

advancing a first catheter into the first blood vessel, wherein the first catheter comprises:

a first catheter body, an electrode, one or more arrays of magnets, and a first plurality of biasing rails, wherein:

the electrode is configured to project from a working site of the first catheter and define an active side of the first catheter;

the one or more arrays of magnets are arranged longitudinally along the first catheter body;

the first plurality of biasing rails longitudinally extend along a length of the first catheter body and are configured to radially arch away from the first catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets; and the first plurality of biasing rails extend from a non-active side of the first catheter body such that the first plurality of biasing rails are configured to bias the working site and the one or more arrays of magnets against a first blood vessel wall; and ablating tissue with the electrode to form the fistula.

21. The method of claim 20, wherein the working site is longitudinally positioned between the proximal point and the distal point.

22. The method of claim 20, further comprising:

advancing a second catheter into the second blood vessel; and aligning the electrode of the first catheter with the second catheter.

23. The method of claim 22, wherein the second catheter comprises a recess, wherein aligning the electrode of the first catheter with the second catheter comprises aligning the electrode with the recess.

24. The method of claim 23, wherein:

the second catheter further comprises a second catheter body and one or more arrays of magnets arranged longitudinally along the second catheter body; and the electrode of the first catheter is aligned with the second catheter via the one or more arrays of magnets of the first catheter and the one or more arrays of magnets of the second catheter.

25. The method of claim 24, wherein the second catheter further comprises:

a second plurality of biasing rails, wherein:

the second plurality of biasing rails longitudinally extend along a length of the second catheter body and are configured to radially arch away from the second catheter body between a proximal point positioned proximal a first end of at least one array of the one or more arrays of magnets of the second catheter and a distal point positioned distal to a second end of the at least one array of the one or more arrays of magnets of the second catheter so as to longitudinally span the at least one array of the one or more arrays of magnets; and the second plurality of biasing rails extend from a non-active side of the second catheter body such that the second plurality of biasing rails are configured to bias the recess and the one or more arrays of magnets of the second catheter against a second blood vessel wall.

26. The method of claim 25, wherein the recess is longitudinally positioned between the proximal point and the distal point.

27. A system for forming a fistula between two blood vessels, comprising:

a first catheter comprising a catheter body, an electrode, one or more arrays of magnets, and a plurality of biasing rails, wherein:

the electrode is configured to project from a working site of the first catheter and define an active side of the first catheter;

the one or more arrays of magnets are arranged longitudinally along the catheter body;

the plurality of biasing rails longitudinally extend along a length of the catheter body;

the plurality of biasing rails are configured to radially arch away from the catheter body between a proximal point positioned proximal a first end of at least one array of the one or more arrays of magnets and a distal point positioned distal to a second end of the at least one array of the one or more arrays of magnets so as to longitudinally span the at least one array of the one or more arrays of magnets;

the plurality of biasing rails extend from a non-active side of the catheter body such that the plurality of biasing rails are configured to bias the working site and the one or more arrays of magnets against a first blood vessel wall;

the plurality of biasing rails are joined by a connecting rail that laterally extends between the plurality of biasing rails at a point between the proximal point and the distal point; and the plurality of biasing rails comprise a proximal portion extending through a lumen of the catheter body, wherein:

the proximal portion may be advanced in the lumen to transition the plurality of biasing rails to an extended configuration, wherein the plurality of biasing rails radially arch away from the catheter body; and the proximal portion may be retracted in the lumen to transition the plurality of biasing rails to a low-profile configuration, wherein a maximum distance of radial deflection of the plurality of biasing rails is less than a maximum distance of radial deflection of the plurality of biasing rails in the extended configuration.

28. The system of claim 27, wherein the plurality of biasing rails are naturally biased from the low-profile configuration to the extended configuration.

29. The system of claim 28, wherein the first catheter further comprises a sleeve configured to be advanced distally to maintain the plurality of biasing rails in the low-profile configuration.

30. The system of claim 27, wherein the plurality of biasing rails are substantially flush with or within the catheter body when in the low-profile configuration.

* * * * *